United States Patent [19]

Weissman

[11] 4,348,183
[45] Sep. 7, 1982

[54] DENTAL POST PROVIDED WITH A RESTORATIVE MATERIAL RETAINER

[75] Inventor: Bernard Weissman, New York, N.Y.

[73] Assignee: IPCO Corporation, White Plains, N.Y.

[21] Appl. No.: 226,783

[22] Filed: Jan. 21, 1981

[51] Int. Cl.³ .............................................. A61C 5/08
[52] U.S. Cl. .................................... 433/221; 433/174
[58] Field of Search ............... 433/221, 220, 173, 174, 433/225; 411/336, 140, 260, 261, 280, 315, 319, 116

[56] References Cited

U.S. PATENT DOCUMENTS

| | | | |
|---|---|---|---|
| 622,670 | 4/1899 | Dwight | 433/221 |
| 631,429 | 8/1899 | Neil | 433/220 |
| 786,748 | 4/1905 | Fordyce | 433/220 |
| 793,269 | 6/1905 | Black | 411/140 |
| 984,782 | 2/1911 | Starr | 433/221 |
| 986,217 | 3/1911 | Rahn | 411/336 |
| 1,942,259 | 1/1934 | Schiemer | 411/336 |
| 2,705,837 | 4/1955 | Gerlach | 433/221 |
| 3,474,537 | 10/1969 | Christensen | 433/174 |
| 3,557,454 | 1/1971 | Whitehill et al. | 433/220 |
| 4,239,489 | 12/1980 | Ellman et al. | 433/220 |

*Primary Examiner*—Gene Mancene
*Assistant Examiner*—John J. Wilson
*Attorney, Agent, or Firm*—Friedman, Goodman & Teitelbaum

[57] ABSTRACT

A holding device for a dental prosthetic structure having an externally threaded elongated post which can be inserted within a bore in a tooth stub. An elongated slot is formed on the outer surface of the post. A retaining nut threads onto the post and includes a plurality of pointed tabs which serve as restorative material retainers. One of the tabs enters into the slot to thereby prevent rotation of the retaining nut with respect to the post. A screw may be threaded into the tooth stub to prevent rotation of the retaining nut relative to the tooth stub.

3 Claims, 7 Drawing Figures

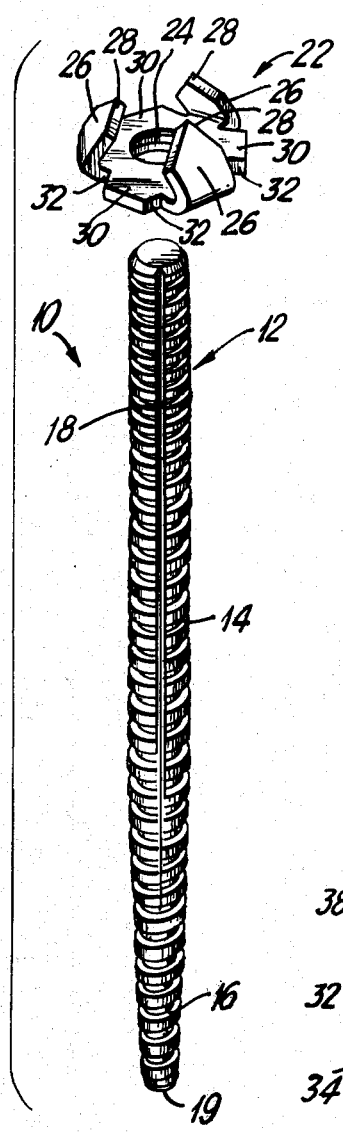
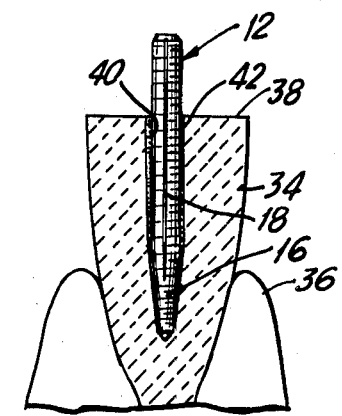
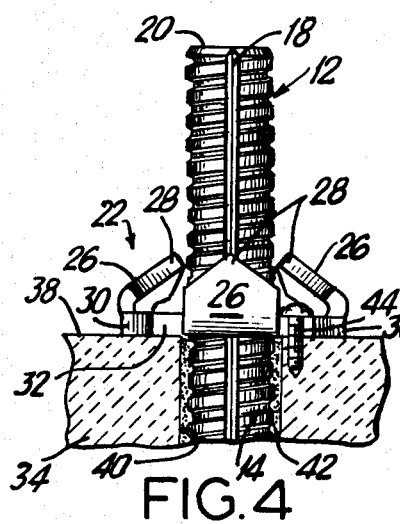
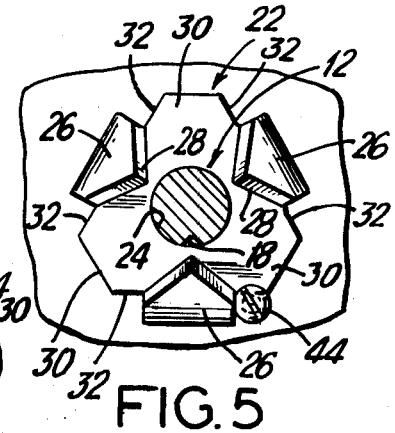
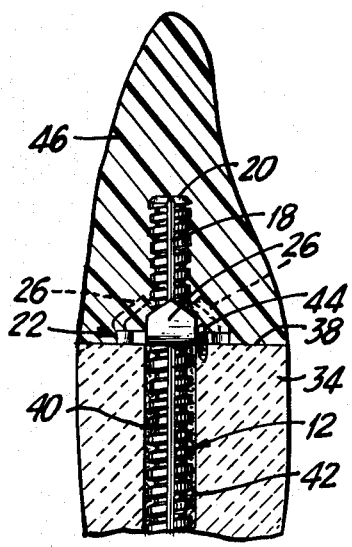
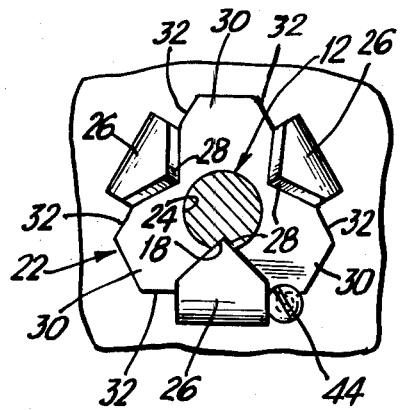

DENTAL POST PROVIDED WITH A RESTORATIVE MATERIAL RETAINER

BACKGROUND OF THE INVENTION

This invention relates to a holding device for a dental prosthetic structure, and more particularly to a dental post provided with a restorative material retainer for connecting a dental prosthetic structure to a tooth stub in a patient's mouth.

A dental prosthetic structure, such as a false tooth, crown or the like, is frequently utilized as an addition to an existing structure in the patient's mouth to replace missing or damaged dentine. In some cases, the prosthetic structure is built upon a tooth stub, while in other cases it is placed on the jaw bone itself. In either case, it is necessary to provide a holding device to securely retain the dental prosthetic structure in suitable position relative to the patient's natural teeth.

Numerous holding devices have been proposed in the prior art. For example, U.S. Pat. No. 3,618,212 describes a dental prosthetic construction having a holding device which secures the structure to the existing tooth by means of a sleeve inserted into the tooth stub with a locking post located in the sleeve and extending upward into the prosthetic structure. Another dental prosthetic assembly is provided in U.S. Pat. No. 3,629,943 which describes a sleeve insertable into the tooth stub having a bent over upper rod portion which enters the sleeve and hooks into the dental prosthetic structure. Still another type of holding device is described in U.S. Pat. No. 3,497,953.

The present device provides a new and novel dental holding device for a dental prosthetic structure which provides a secure retention of the prosthetic structure and a secure holding of the dental restorative material with respect to the existing tooth stub.

SUMMARY OF THE INVENTION

It is accordingly an object of the present invention to provide a holding device for a dental prosthetic structure which provides improved and simplified utilization over the prior art.

Another object of the present invention is to provide a dental post with a restorative material retainer which can be utilized for holding a dental prosthetic structure with respect to a patient's tooth stub, jaw bone or the like.

Still another object of the present invention is to provide a holding device for a dental prosthetic structure which permits the structure to be firmly secured to an existing tooth stub.

Another object of the present invention is to provide the use of substantially preformed standardized members wherein the dental prosthetic structure is securely retained with such standardized members for conformed securement with respect to the tooth stub.

Yet another object of the present invention is to provide a holding device for a dental prosthetic structure which provides simplified utilization and facilitates simple assembly to the patient's tooth stub.

Briefly, in accordance with the present invention, there is provided a holding device for a dental prosthetic structure including an externally threaded elongated post having an elongated slot formed into the outer surface thereof. A portion of the post is securely inserted within a conformally shaped bore in a tooth stub. A retaining nut is provided which can be threaded onto the post and includes a plurality of inwardly directed, upwardly extending pointed tabs about its periphery. The tabs provide anchoring within the dental restorative material of the dental prosthetic structure. The tabs are deformable so as to permit the tab which is closest to the slot to be deformed so as to enter into the slot thereby preventing rotation of the retaining nut with respect to the post. The remainder of the post, as well as the retaining nut, can then be secured within the dental restorative material of the dental prosthetic structure. Additionally, a screw can be threaded into the tooth stub to prevent rotation of the retaining nut relative to the tooth stub.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which:

FIG. 1 is an exploded perspective view of the holding device in accordance with the present invention;

FIG. 2 is a cross sectional view taken through a tooth stub, showing a first step to prepare the tooth stub for utilization of the holding device of the present invention.

FIG. 3 is a view similar to that shown in FIG. 2, showing a further step which includes the elongated post inserted within the tooth stub;

FIG. 4 is an enlarged cross sectional view showing the positioning of the holding device within the tooth stub;

FIG. 5 is a top view showing the retainer nut threaded onto the elongated post;

FIG. 6 is a view similar to that of FIG. 5, showing the retainer nut locked in place with respect to the post, and FIG. 7 is a cross sectional view showing the holding device of the present invention retaining a dental prosthetic structure onto a tooth stub.

In the various figures of the drawings, like reference characters designate like parts.

DETAILED DESCRIPTION OF THE PREFERRED EMBODIMENT

With reference now to FIG. 1, the holding device of the present invention is shown generally at 10 and includes an elongated post 12 having an external helical thread 14 formed about its outer surface. The lower end portion 16 of the post is slightly tapered. An elongated slot 18 is axially formed into the outer surface of the post 12 and cuts into the grooves of the thread. The slot 18 commences at the upper end 20 and extends along substantially a major length of the post into the tapered lower end portion 16, the slot 18 being spaced from the lower end 19 of the post.

A retaining nut 22 has an internally threaded central bore 24 for threading of the nut onto the post 12. From the periphery of the nut 22, there are provided a plurality of inwardly directed, upwardly extending tabs 26 having their distal ends shaped into points 28. Three such tabs 26 are shown.

Spaced between adjacent tabs 26, there are provided protruding sections 30 which terminate with inwardly extending shoulders 32 adjacent each of the tabs, as can best be seen in FIG. 5.

With reference now to FIGS. 2-4, the assembly of the present invention with respect to a prosthetic structure will now be described. Initially, the tooth stub 34 extending from the gum base 36 is prepared by suitably forming its upper edge 38 so as to be able to receive a dental prosthetic structure, in accordance with standard conventional techniques. A bore 40 is formed into the tooth stub 34 having a lowered tapered end 42. The bore is formed slightly larger than the post so that the post can be easily inserted into the stub, as shown in FIG. 3.

Suitable dental anchoring material 42 is placed about the post 12 in the bore 40 so as to anchor the post in the bore. The anchoring can be provided by cementing, using well known dental cement materials. The threads 14 about the periphery of the post 12 provide additional retaining of the post in the bore 40 since the cement 42 will suitably position itself within the threads 14 to prevent the post 12 from being pulled out of the bore 40. Similarly, the cement 42 will also position itself in the slot 18, so that when the post 12 is securely embedded, the post 12 will be prevented from rotating within the bore 40.

After suitably cementing the post 12 in the tooth stub 34, the retaining nut 22 is threaded onto the extending free portion of the post. The retaining nut is positioned far enough down the post so that it proximately sits upon the upper surface 38 of the tooth stub 34. The positioning of the retaining nut can best be seen with respect to FIGS. 4 and 5.

The retaining nut 22 is then adjusted so that one of the inwardly directed tabs 26 is positioned adjacent to and in alignment with the slot 18, as shown in FIGS. 4 and 5. The tabs 26 are deformable to permit the particular tab closest to the slot 18 to be inwardly bent so that its pointed end 28 will enter into the slot 18 and provide a positive lock between the retaining nut 22 and the post 12 to prevent relative rotation therebetween. Such positioning can best be seen in FIG. 6.

The tabs 26 themselves serve as restorative material retainers to securely hold the restorative material in the prosthetic structure when formed thereon, as set forth below. The tabs 26 accordingly act as an anchor in the restorative material.

At the same time, one of the tabs, specifically the tab within the slot, is also utilized to provide a positive lock between the retainer nut and the post to prevent rotation therebetween, as set forth above. The remaining two tabs need not be deformed so that they can best act as an anchor for the restorative material.

As set forth above, the slot 18 formed in the post also serves a double purpose. The slot prevents the post from moving within the bore by receiving cement therein, and it also acts as a receiving member for the tab thereby preventing rotation of the retaining nut with respect to the post.

Should additional retention be required, a further stop member can be provided, such as a screw 44 being threaded into the tooth stub 34 and positioned between any one of the shoulders 32 and the bottom portion of the adjacent tab. The screw 44 will then further prevent the retaining nut 22, and the post 12 secured thereto, from rotating with respect to the tooth stub 34. Thus, the stop member will reinforce the engagement of the cement in the slot 18 to prevent rotation therebetween. The stop member can be the screw 44 with a head as shown, or could also be any other type of stop member including pins, anchors, etc.

As is best seen in FIG. 7, once the post 12 has been suitably anchored within the tooth stub 34 and the retaining nut 22 has been positioned in place with the locking tab bent into the slot 18, the prosthetic structure can then be built up using dental restorative material, and utilizing conventional dental procedures, as is well known. The prosthetic structure is shown as a false crown 46. The upper end of the post 12, as well as the retaining nut 22, will be suitably encased within the prosthetic structure 46 so as to securely retain the prosthetic structure 46 in place on the tooth stub 34.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A holding device for a dental prosthetic structure, said holding device comprising:

an elongated post for secured insertion within a conformally shaped bore in a tooth stub, said post including securing means on one end portion thereof for coacting with cement for securely retaining said post within the bore in the tooth stub;

said securing means including first external thread means for receiving the cement therein to prevent said post from being pulled out of the bore, said securing means further including first slot means disposed longitudinally along said one end portion of said post and across said first thread means for receiving the cement therein to prevent relative rotation between said post and the tooth stub;

retaining means disposed on the opposite end portion of said post for anchoring dental restorative material of the dental prosthetic structure on the tooth stub, said retaining means including a retaining member provided with a centrally disposed, threaded opening therethrough for receiving said opposite end portion of said post therein;

said opposite end portion of said post including second external thread means coacting with said threaded opening of said retaining member to threadedly secure said retaining member on said opposite end portion of said post;

said post being threaded along its length to define said first and second external thread means;

said retaining member including anchoring means extending outwardly therefrom for securement within the dental restorative material, said anchoring means including a plurality of inwardly directed, upwardly extending tabs, said tabs being spaced apart about said retaining member, said tabs having pointed free end portions, said tabs being an integral part of said retaining member; and cooperative locking means on said opposite end portion of said post and said retaining member for positionally stabilizing said retaining member with respect to said post to prevent rotation of said retaining member relative to said post, said locking means including second slot means disposed longitudinally along said opposite end portion of said post, said opposite end portion being disposed between said tabs within the dental restorative material, said locking means further including a selected one of said tabs, each of said tabs being deformable to permit entry of said selected one into said second slot means to thereby prevent the rotation of said retaining member with respect to said post;

said post including a longitudinally extending slot to define said first and second slot means.

2. A holding device as in claim 1, wherein said retaining member has a plurality of shoulders about its periphery, and further comprising stop means for positioning in the tooth stub adjacent at least one of said shoulders for directly preventing rotation of said retaining member relative to the tooth stub.

3. A holding device as in claim 1, wherein said one end portion of said post includes a tapered end.

* * * * *